(12) United States Patent
Sun et al.

(10) Patent No.: US 6,922,279 B2
(45) Date of Patent: Jul. 26, 2005

(54) HARMONIC GENERATION MICROSCOPY

(75) Inventors: Chi-Kuang Sun, Taipei (TW); Shi-Wei Chu, Taipei (TW)

(73) Assignee: National Taiwan University, Taipei (TW)

( * ) Notice: Subject to any disclaimer, the term of this patent is extended or adjusted under 35 U.S.C. 154(b) by 115 days.

(21) Appl. No.: 10/665,443

(22) Filed: Sep. 20, 2003

(65) Prior Publication Data

US 2005/0063041 A1 Mar. 24, 2005

(51) Int. Cl.$^7$ .............................. G02F 1/37; G01B 9/04
(52) U.S. Cl. ...................... 359/329; 359/328; 359/381; 356/904
(58) Field of Search ................................ 359/326–332, 359/368–373, 381; 356/904

(56) References Cited

U.S. PATENT DOCUMENTS

| | | | |
|---|---|---|---|
| 4,063,804 A | * 12/1977 | Hellwarth et al. | .......... 359/352 |
| 5,828,459 A | 10/1998 | Silberberg | .................. 356/444 |
| 6,208,886 B1 | 3/2001 | Alfano et al. | ............... 600/473 |
| 6,693,257 B1 | * 2/2004 | Tanaka | .................. 219/121.76 |
| 2004/0135079 A1 | * 7/2004 | Moellmann | .................. 250/234 |

OTHER PUBLICATIONS

Two–Photon Laser Scanning fluorescence Microscopy Winfried Denk, James H. Strickler and Watt W. Webb, Science, New Series, vol. 248, Issue 4951 (Apr. 6, 1990), pp 73–76.
Second–harmonic imaging in the scanning optical microscope J. N. Gannaway and C. J. R. Sheppard, Optic Quantum Electron, 1978, vol. 10, pp. 435–439.
Nonlinear scanning laser microscopy by third harmonic generation Y. Barad, H. Eisenberg, M. Horowitz and Y. Silberberg, Applied Physics Letters, 1997, vol. 70, pp 922–924.

* cited by examiner

*Primary Examiner*—John D. Lee

(57) ABSTRACT

A harmonic generation microscopy employs a laser device that emits a laser beam having a predetermined wavelength that causes no autofluorescence in a biological sample and that, after excited, induces both the second and third harmonic waves. The laser beam is projected onto a sample and an observation beam from the sample is received. The observation beam is directed through a splitter to separate the second harmonic wave and the third harmonic wave both of which are then converted into corresponding electrical signals. The electrical signals are fed to a computer-based image processing equipment to form an image of the sample on the basis of the second and third harmonic waves.

21 Claims, 6 Drawing Sheets

HARMONIC GENERATION MICROSCOPY

BACKGROUND OF THE INVENTION

1. Field of the Invention

The present invention relates generally to the field of harmonic generation microscopy, and in particular to a microscopic imaging technique using both second and third harmonic waves of a excitation spectrum of a laser beam by a sample to form an image of the sample.

2. The Related Art

Microscopic imaging has been widely used in a variety of applications. For example, microscopic observation of a biological tissue is one of the best-known applications of the microscopic imaging techniques. The recent development of the microscopic imaging allows for the employment of laser beam in high precision observation of biological samples. An example of the laser-based microscopy is two-photon laser scanning fluorescent microscopy that was published in *Science*, New Series, Volume 248, Issue 4951 (Apr. 6, 1990), pp 73–76, by Winfried Denk, James H. Strickler and Watt W. Webb. A biological sample is stained by a fluorescent dye. The fluorescent dye molecule is excited by simultaneously absorbing two photons of the same wavelength to give off fluorescent light, which is received and processed for imaging of the biological sample. In this respect, this technique is also applicable to autofluorescent biological samples. The image obtained with the two-photon fluorescent microscopy has excellent resolution. However, the fluorescent dye may be toxic to in vivo samples. Further, the excitation of the fluorescent light by absorption of photons may induce photo-damages to the observed samples. For example, with a Ti: Sapphire laser having a pulse duration 100 fs and a repetition rate of 80 MHz, an average power exceeding 6 mW causes photo-damage to the samples.

Contrary to the fluorescent microscopy, a harmonic generation microscopy induces less photo-damage to the samples. The most commonly known harmonic generation microscopy includes second harmonic generation (SHG) microscopy and third harmonic generation (THG) microscopy.

SHG that was originally employed in the research of second harmonic generation crystals has recently been used in the observation of noncentrosymmetric biological samples, such as "Second-Harmonic Imaging in the Scanning Optical Microscope" by J. N. Gannaway and C. J. R. Sheppard (1978), *Optic Quantum Electron*, Volume 10, pp. 435–439. SHG often occurs in a noncentrosymmetric and continuous structured media, especially nano-structures, such as stacked membranes, aligned protein structures, and microtubule arrays. However, SHG is not suitable for the observation of interfaces in biological samples.

THG microscopy was first published in *Applied Physics Letters*, 1997, Volume 70, pp. 922–924 by Y. Barad, H. Eisenberg, M. Horowltz and Y. Silberberg, which is employed in the observation of transparent media by means of the third harmonic generation occurring in the interface. Since all materials have non-varnishing third order coefficient and since the coefficient is different at different portions of an observed sample, which induces variation of THG intensity, the THG microscopy is commonly used in non-linear scanning microscopic imaging process. Since THG often occurs in the interface, THG is not suitable for observation of bulk noncentrosymmetric media, which, however, can be clearly inspected by means of SHG.

An example of the THG microscopy is disclosed in U.S. Pat. No. 5,828,459.

A similar technique is disclosed in U.S. Pat. No. 6,208,886, which uses a laser source, such as Ti: Sapphire laser, Cr: Forsterite laser and Nd: Yag laser, to issue a laser beam having a wavelength within the range of 400–1400 nm. The radiation excites the observed sample to give off fluorescent light and third harmonic wave. Due to the generation of the fluorescent light, photo-damage is inherent in this technique. Further, due to lacking of the second harmonic wave, noncentrosymmetric object cannot be well examined by this technique.

Apparently, the conventional microscopic imaging techniques discussed above have one or more drawbacks in providing clear and wide range observation of a sample.

SUMMARY OF THE INVENTION

Therefore, a primary object of the present invention is to provide a harmonic generation microscopy that eliminates photo-damage to the observed samples.

Another object of the present invention is to provide a harmonic generation microscopy that uses both second harmonic generation and third harmonic generation at the same time to provide a clear image comprising both a continuous noncentrosymmetric structure and an interface of the structure.

To achieve the above objects, in accordance with the present invention, there is provided a harmonic generation microscopy which employs a laser device that emits a laser beam having a predetermined wavelength that causes no autofluorescence in a biological sample and that, after excited, induces both the second and third harmonic waves. The laser beam is projected onto a sample and an observation beam from the sample is received. The observation beam is directed through a splitter to separate the second harmonic wave and the third harmonic wave both of which are then converted into corresponding electrical signals. The electrical signals are fed to a computer-based image processing equipment to form an image of the sample on the basis of the second and third harmonic waves.

BRIEF DESCRIPTION OF THE DRAWINGS

The present invention will be apparent to those skilled in the art by reading the following description of a best mode for carrying out the invention and a preferred embodiment of a microscopic imaging system employed in the present invention, with reference to the attached drawings, in which.

DETAILED DESCRIPTION OF THE BEST MODE FOR CARRYING OUT THE INVENTION AND THE PREFERRED EMBODIMENT THEREOF

Figure 1:
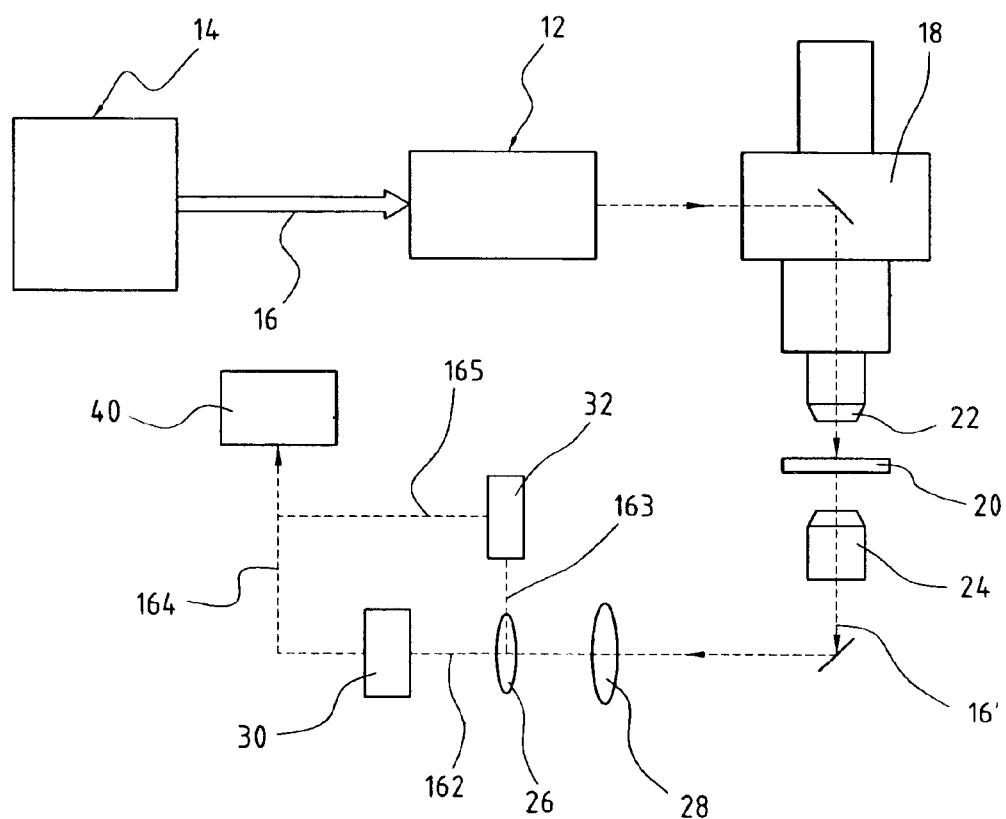
FIG. 1 is a block diagram of a microscopic imaging system in accordance with the present invention.

With reference to the drawings and in particular to FIG. 1, a microscopic imaging system in accordance with the present invention, generally designated with reference numeral 10, comprises a scanning device 12 that receives a laser beam 16 from a laser device or laser source 14, such as a short pulse laser device. Optic elements, such as a mirror array (not shown) capable of two-dimensional rotation, are included in the scanning device 12 for directing the laser beam 16 into a microscope 18.

A sample 20 to be observed is positioned in the microscope 18. The sample can be any suitable ones, such as a biological sample on a glass plate. This in known to those having ordinary skills in the field of biology and thus no further detail is needed herein.

The laser beam 16 that is directed into the microscope 18 by the scanning device 12 is focused by an objective lens 22 of the microscope 18 onto the sample 20, which induces an observation beam 16' by letting the laser beam 16 transmitting therethrough or reflecting the laser beam 16. A focusing lens 24 receives and projects the observation beams 16' to an optic system comprised of splitter, which will be further described. The focusing lens 24 may be separate from the objective lens 22 as shown in the drawings or, alternatively, the objective lens 22 and the focusing lens 24 can be the same lens.

The scanning device 12 can be the one that is capable to selectively guide the laser beam 16 to perform a two-dimensional scanning operation on the sample 20 to form a sectioned image of the sample 20. Alternatively, the scanning device 20 comprises means for moving the sample to form two- or three-dimensional scanning operation. In the embodiment illustrated, the laser source 14 comprises a laser device that generates a laser beam that, after excited, induces remarkable second harmonic wave ($\lambda/2$) and third harmonic wave ($\lambda/3$). An example of the laser source 14 is Cr: Forsterite laser, having a pulse wavelength within the range of 1200–1350 nm. Preferably, the wavelength of the laser beam 16 is 1230 nm. Within this range, the excitation spectrum of the laser beam issued by Cr: Forsterite laser shows clear and distinct second and third harmonic waves in the range of visible light. It is noted that the laser beam from Cr: Forsterite laser does not cause autofluorescence, or little autofluorescence if any, on the sample within this wavelength range. Contrary to the conventional fluorescent microscopy that employs fluorescent light for observation purposes, the harmonic generation microscopy of the present invention causes much reduced toxic effect or photo-damage to an in vivo sample. Thus, the present invention is most suitable for the observation of cell structure and living tissues.

Another range of the wavelength that can be employed in the present invention is 1600–2000 nm.

In addition, the laser beam within this range of wavelength allows for deep penetration into the observed sample. Thus, clearer image of the sample can be obtained.

Figure 2:
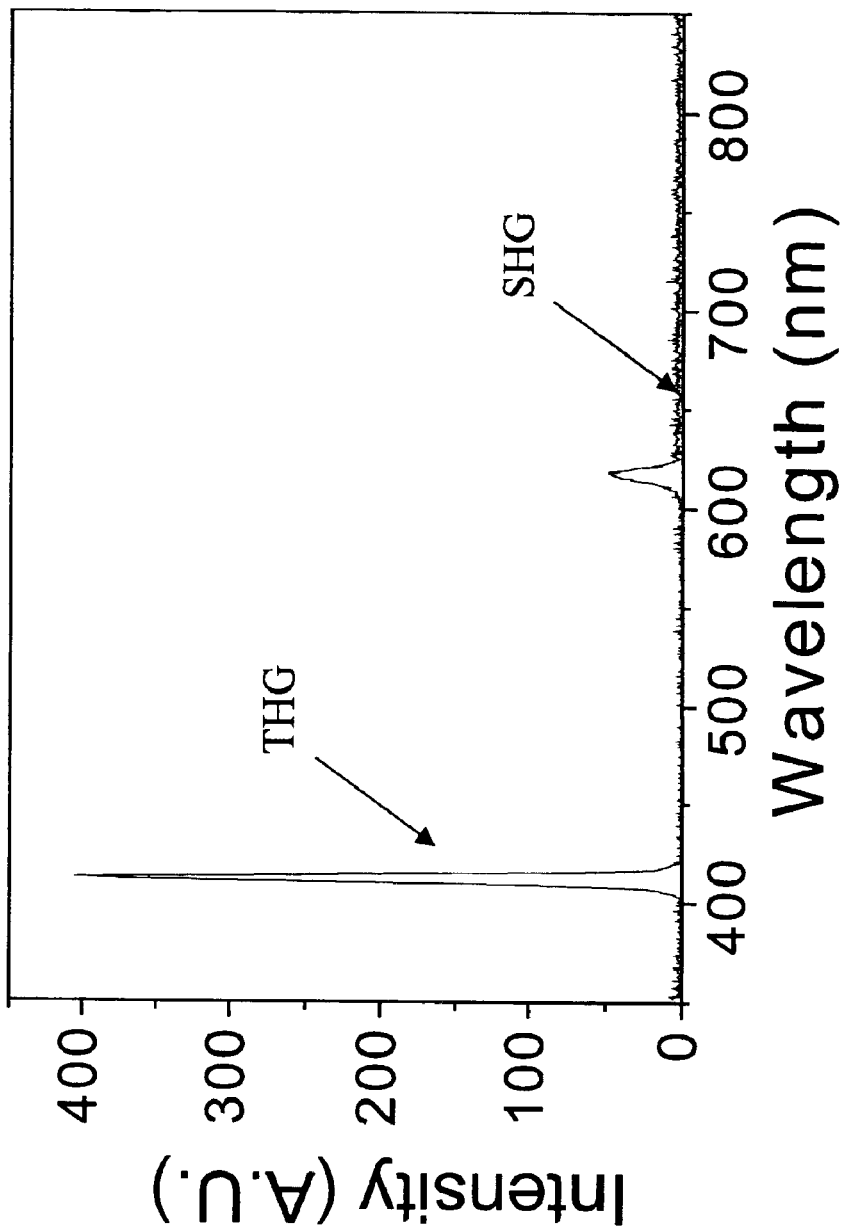
FIG. 2 is a plot of excitation spectrum of a laser beam employed in the microscopic imaging system of the present invention.
Figure 3:
FIGS. 3–6 are pictures showing observation of Zebrafish egg cleavage at different stages by means of SHG microscopy (left hand side picture, marked SHG), THG microscopy (middle picture, marked THG) and the harmonic generation microscopy in accordance with the present invention (right hand side picture, marked SHG+THG).
Figure 3:
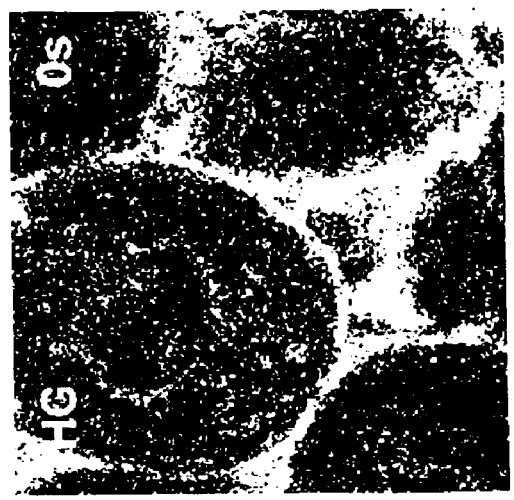
Figure 3:
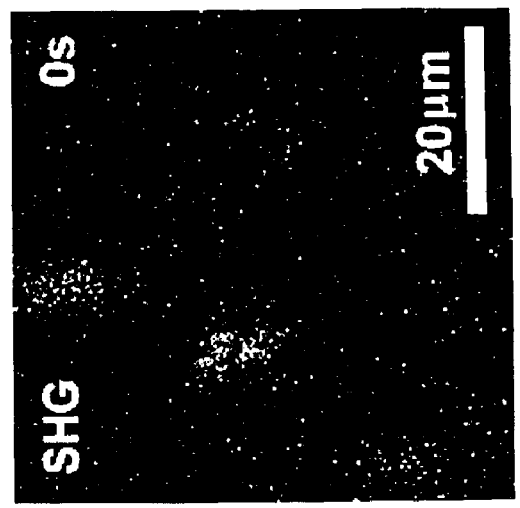
Figure 4:
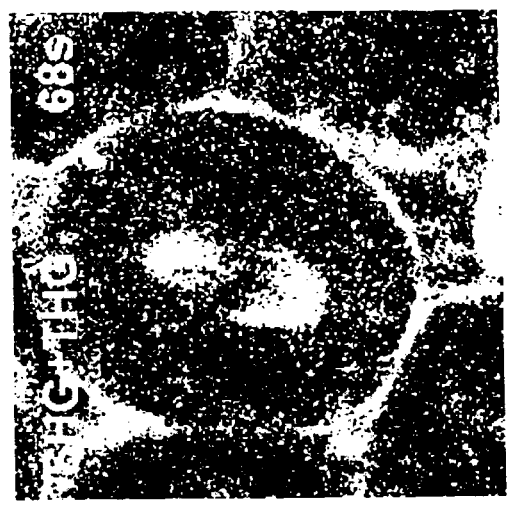
Figure 4:
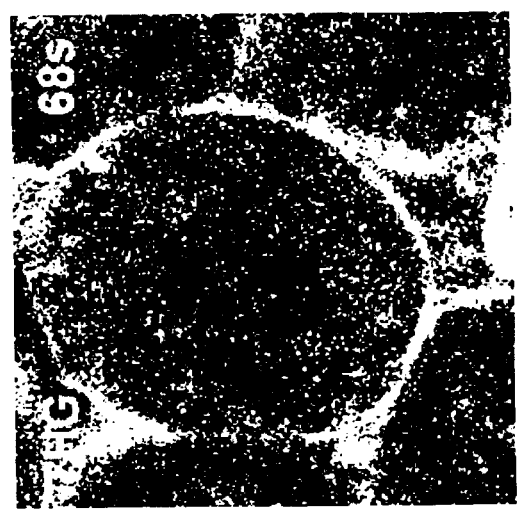
Figure 4:
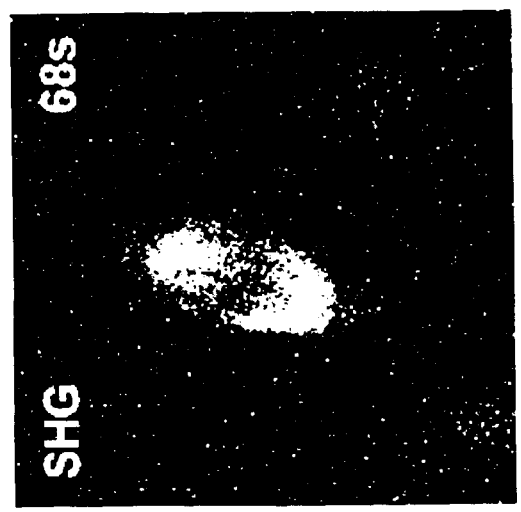
Figure 5:
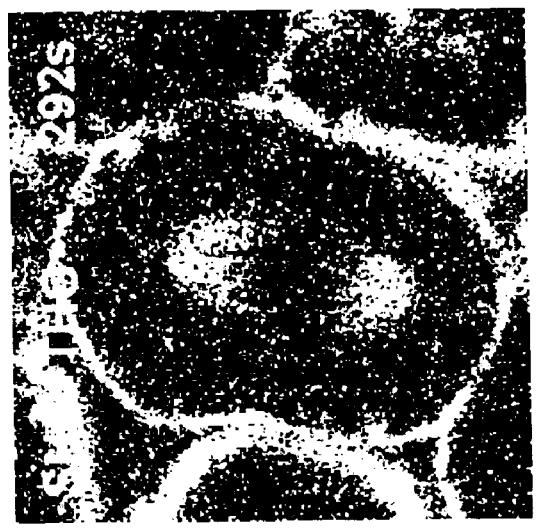
Figure 5:
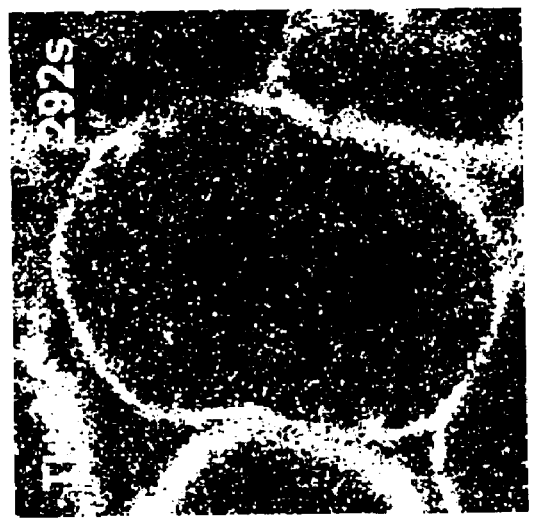
Figure 5:
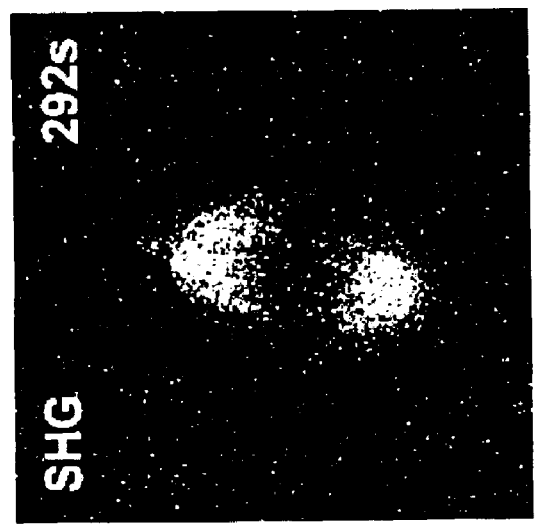
Figure 6:
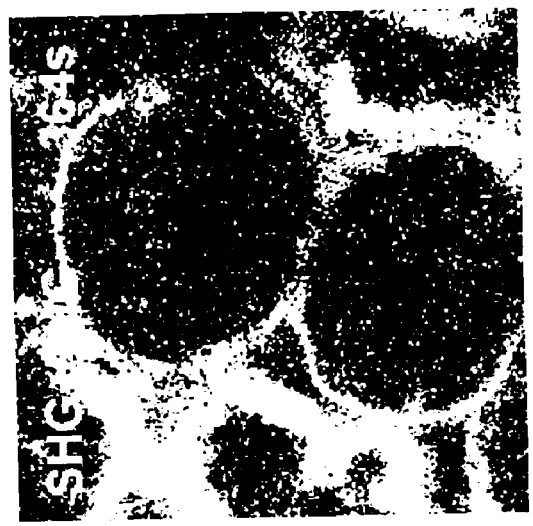
Figure 6:
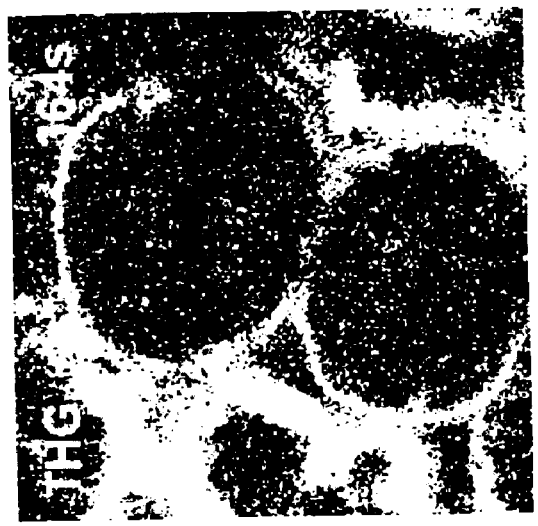
Figure 6:
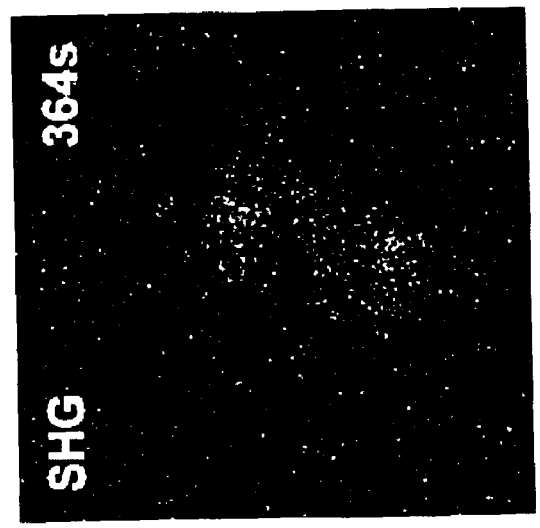

FIG. 2 shows a plot of excited spectrum obtained from the sample 20 after being irradiated by the laser beam 16. The plot clearly reveals that the second (SHG) and third (THG) harmonic waves can be clearly observed in accordance with the present invention.

The observation light 16' that is received by the focusing lens 24 comprises the second harmonic wave and the third harmonic wave. The observation light 16' is guided through a lens 28 toward a splitter 26. The second harmonic wave component 162 and the third harmonic wave component 163 of the observation light 16' are separated from each other by the splitter 26. For example, the splitter 26 may allow for transmission of the second harmonic wave component 162 therethrough, while refracts the third harmonic wave component to a different direction, as shown in the drawings.

Alternatively, the third harmonic wave component 163 may be allowed to directly transmit through the splitter 26, while the second harmonic wave component 162 is directed to another direction.

The second and third harmonic wave components 162, 163 that are separated by the splitter 26 are respectively directed to photo-electronic devices, such as photo detectors 30, 32, and are converted into corresponding electrical signals 164, 165 by the photo detectors 30, 32. The electrical signals 164, 165 are then applied to a computer system 40 and processed thereby to generate and display an image of the sample 20. Since image processing is well known and is not the feature of the present invention, no further detail will be given herein.

Thus, the present invention provides a harmonic generation microscopy comprising the following steps: (1) A laser source is selected, which gives off a laser beam having a wavelength within a predetermined range that does not cause autofluorescence on an observed sample and that is capable to induce both the second harmonic generation and third harmonic generation, after the sample is excited. (2) A microscope is employed to project the laser beam onto the sample and an observation beam induced by the laser beam transmitting through or reflected by the sample is collected. (3) The observation beam is directed through splitting means to have a second harmonic wav component and a third harmonic wave component of the observation beams separated from each other. (4) The second and third harmonic wave components are converted into corresponding electrical signals. (5) The electrical signals are applied to and processed by a computer system to form an image of the sample.

If desired, the harmonic generation microscopy of the present invention further comprises a step of performing a two-dimensional scanning with the laser beam in the sample to obtain sectioned image of the sample.

Since some of the conventional optic microscopes are operated with fluorescent light or a combination of the fluorescent light and one of the second harmonic generation and the third harmonic generation, staining a sample to be observed is inevitable. Toxic effect by the dye and photo-damage to the sample often occur. On the contrary, the present invention uses a laser beam in the wavelength range of 1200–1350 nm, which does not excite autofluorescence of most animal tissue sample and has a deep penetration into the sample and low photo-damages. The present invention also makes use of both the second and third harmonic generation to provide a clear image of both a continuous noncentrosymmetric structure of a sample and an interface thereof thereby serving as a useful non-invasion observation tool for in vivo samples.

To this point, it is apparent that the present invention has the following advantages:

(1) No dying agent is needed and the sample is observed by means of harmonic generation of laser beam. Thus, damage to in vivo sample is substantially eliminated.

(2) The laser beam employed by the present invention has a wavelength within a predetermined range, which does not generate fluorescent light or little fluorescent light if any. The present invention allows for clear observation of a sample without generation of fluorescent light and images of the sample is obtained by means of both the second and third harmonic generation.

The laser beam is selected to have a deep penetration into the sample whereby details inside the sample can be obtained.

An experiment of using the harmonic generation microscopy of the present invention to observe Zebrafish egg cleavage is demonstrated in FIGS. 3–6, which correspond, in sequence, to different stages of the cleavage. Each of FIGS. 3–6 comprises three pictures, of which the left had side picture is obtained by SHG microscopy (marked SHG), the middle picture by THG microscopy (marked THG) and the right handle side picture by the harmonic generation microscopy of the present invention (marked SHG+THG). Clear enough, the SHG+THG picture is a combination of the SHG picture and the THG picture. More information can be obtained with a single picture taken in accordance with the present invention than those taken with the conventional methods.

Although the present invention has been described with reference to the best mode for carrying out the present invention and a preferred embodiment of an associated system, it is apparent to those skilled in the art that a variety of modifications and changes may be made without departing from the scope of the present invention which is intended to be defined by the appended claims.

What is claimed is:

1. A microscopic imaging system comprising:
   a laser device giving off a laser beam having a predetermined wavelength;
   a microscope receiving the laser beam and projecting the laser beam to an observed sample to obtain an observation beam;
   splitting means for splitting the observation beam into a second harmonic wave component and a third harmonic wave component; and
   detection means for detecting the second and third harmonic wave components and, in response thereto, generating first and second electrical signals corresponding to the second and third harmonic wave component.

2. The microscopic imaging system as claimed in claim 1 further comprising a computer system that receives and processes the first and second electrical signals to form an image of the sample.

3. The microscopic imaging system as claimed in claim 1, wherein the predetermined wavelength is within a range of 1200–1350 nm.

4. The microscopic imaging system as claimed in claim 3, wherein the predetermined wavelength is 1230 nm.

5. The microscopic imaging system as claimed in claim 1, wherein the predetermined wavelength is within a range of 1600–2000 nm.

6. The microscopic imaging system as claimed in claim 1, wherein the laser device comprises a Cr: Forsterite laser.

7. The microscopic imaging system as claimed in claim 1 further comprising scanning means for guiding the laser beam to perform a two-dimensional scanning operation on the sample.

8. The microscopic imaging system as claimed in claim 1 further comprising scanning means for moving the sample to form a two-dimensional/three-dimensional scanning operation.

9. The microscopic imaging system as claimed in claim 1 further comprising a focusing lens for directing the observation beam to the splitting means.

10. The microscopic imaging system as claimed in claim 1, wherein the laser device comprises a short pulse laser.

11. The microscopic imaging system as claimed in claim 1, wherein the wavelength of the laser beam causes no autofluorescence on the sample.

12. A harmonic generation microscopy comprising the following steps:
    (1) providing a laser device that gives off a laser beam having a predetermined wavelength;
    (2) providing a microscope that receives and projects the laser beam onto an observed sample to obtain an observation beam comprised of a second harmonic wave component and a third harmonic wave component;
    (3) splitting the second harmonic wave component and the third harmonic wave component from each other; and
    (4) converting the second harmonic wave component and the third harmonic wave component into first and second electrical signals respectively; and
    (5) processing the first and second electrical signals to form an image of the sample.

13. The harmonic generation microscopy as claimed in claim 12, wherein the first and second electrical signals are processed by a computer system to form the image of the sample.

14. The harmonic generation microscopy as claimed in claim 12, wherein the predetermined wavelength is within a range of 1200–1350 nm.

15. The harmonic generation microscopy as claimed in claim 14, wherein the predetermined wavelength is 1230 nm.

16. The harmonic generation microscopy as claimed in claim 12, wherein the predetermined wavelength is within a range of 1600–2000 nm.

17. The harmonic generation microscopy as claimed in claim 12, wherein the laser device comprises a Cr: Forsterite laser.

18. The harmonic generation microscopy as claimed in claim 12 further comprising a step of guiding the laser beam to perform a two-dimensional scanning operation on the sample.

19. The harmonic generation microscopy as claimed in claim 12 further comprising a step of moving the sample to form a two-dimensional/three-dimensional scanning operation on the sample.

20. The harmonic generation microscopy as claimed in claim 12, wherein the laser device comprises a short pulse laser.

21. The harmonic generation microscopy as claimed in claim 12, wherein the wavelength of the laser beam causes no autofluorescence on the sample.

* * * * *